United States Patent

Shibata et al.

Patent Number: 4,959,173
Date of Patent: Sep. 25, 1990

[54] OPTICALLY ACTIVE ESTER COMPOUND

[75] Inventors: Toshihiro Shibata, Saitama; Norio Kurosawa, Tokyo; Masaki Kimura, Saitama, all of Japan

[73] Assignee: Adeka Argus Chemical Co., Ltd., Tokyo, Japan

[21] Appl. No.: 242,177

[22] Filed: Sep. 8, 1988

[30] Foreign Application Priority Data

Sep. 29, 1987 [JP] Japan ................... 62-244780
Jan. 8, 1988 [JP] Japan ................... 63-2226
Apr. 1, 1988 [JP] Japan ................... 63-81609

[51] Int. Cl.$^5$ .............................. C09K 19/12
[52] U.S. Cl. .................. 252/299.65; 252/299.01; 560/59
[58] Field of Search ........... 350/350.5; 252/299.01, 252/299.65; 560/59

[56] References Cited

U.S. PATENT DOCUMENTS

| | | | |
|---|---|---|---|
| 4,136,053 | 1/1979 | Steinstrasser et al. | 252/299.65 |
| 4,149,413 | 4/1979 | Gray et al. | 252/299.65 |
| 4,257,911 | 3/1981 | Gray et al. | 252/299.65 |
| 4,596,667 | 6/1986 | Inukai et al. | 252/299.65 |
| 4,613,209 | 9/1986 | Goodby et al. | 350/350.5 |
| 4,614,609 | 9/1986 | Inoue et al. | 252/299.65 |
| 4,710,585 | 12/1987 | Taguchi et al. | 252/299.65 |
| 4,786,730 | 11/1988 | Shibata et al. | 252/299.01 |
| 4,801,756 | 2/1989 | Kano et al. | 252/299.01 |
| 4,804,759 | 2/1989 | Shibata et al. | 252/299.01 |
| 4,834,907 | 5/1989 | Troue et al. | 252/299.65 |
| 4,880,560 | 11/1989 | Yoshinaga et al. | 252/299.01 |
| 4,886,622 | 12/1989 | Miyazawa et al. | 252/299.61 |
| 4,886,623 | 12/1989 | Mitsuhashi et al. | 252/299.65 |
| 4,911,861 | 3/1990 | Higuchi et al. | 252/299.65 |
| 4,911,863 | 3/1990 | Sage et al. | 252/299.65 |
| 4,913,838 | 4/1990 | Miyazawa et al. | 252/299.61 |
| 4,918,213 | 4/1990 | Nohira et al. | 558/271 |

Primary Examiner—John S. Maples
Assistant Examiner—Richard Treanor
Attorney, Agent, or Firm—Young & Thompson

[57] ABSTRACT

An optically active ester of the formula

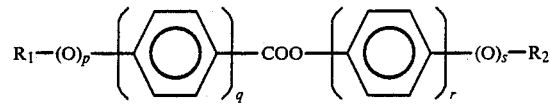

wherein p is 0 or 1, q is 1 or 2, r is 1 or 2, q+r is 3, and s is 0 or 1. $R_1$ and $R_2$ in the above formula are each independently selected from the group consisting of $C_{6-18}$ straight chain alkyl and an optically active group of the formula

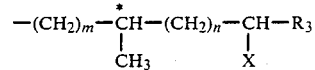

and in which m is 2 to 5, n is 1 or 2, X is hydrogen or chlorine, $R_3$ is hydrogen or $C_{1-11}$ straight chain alkyl, and C* represents a chiral carbon atom, with the proviso that when n is 1 and X is hydrogen, $R_3$ is $C_{1-11}$ straight chain alkyl. When q is 2 and r is 1 and $R_1$ is $C_{6-18}$ straight chain alkyl, p is 1; on the other hand, when q is 1 and r is 2 and $R_2$ is an optically active group of the above formula, s is 1. One of $R_1$ and $R_2$ is an optically active group of the above formula, and the other of $R_1$ and $R_2$ is $C_{6-18}$ straight chain alkyl.

10 Claims, No Drawings

OPTICALLY ACTIVE ESTER COMPOUND

BACKGROUND OF THE INVENTION

1 Field of the Invention

This invention relates to an ester compound containing optically active alkyl or alkoxy group in the molecule, which is useful as a ferroelectric liquid crystal compound.

2 Description of the Prior Art:

Methods of displaying with a liquid crystal display element widely used today may be classified into those of twisted nematic (TN) and dynamic scattering (DS) types. These methods involve nematic liquid crystal cells comprising nematic liquid crystals as the main component. One of the disadvantages of conventional nematic liquid crystal cells is that their response speed is of the order of several milliseconds at the most, which cosiderably restrict the application thereof. It has been recently found that a higher response speed can be obtained by using a smectic liquid crystal cell.

It has been disclosed that some optically active smectic liquid crystals show ferroelectricity and thus the application thereof has been eagerly expected. An example of the ferroelectric liquid crystals is 2-methylbutyl-4-(4-n-decyloxy-benzylidenamino) cinnamate which will be abbreviated to DOBAMBC hereinafter. This compound is characterized by showing a ferroelectricity in the chiral smectic phase which will be abbreviated to Sc* phase hereinafter.

Since it was found that a DOBAMBC film cell had a high response speed of the order of a microsecond, this ferroelectric liquid crystal compound has attracted public attention as a material available not only in display devices of, for example, a liquid crystal TV but also in various optoelectronics devices such as a photoprinter head, an optical Fourier-transform element and a light valve.

However the DOBAMBC has not been utilized in practice yet, since it is chemically unstable because of the presence of a Schiff base structure therein.

Recently, optically active ester compounds such as alkoxybiphenylcarboxylic acid alkoxyphenyl esters and alkoxybenzoic acid alkoxybiphenyl esters which contain an optically active alkoxy group such as 2-methylbutoxy, 6-methyloctoxy and 1-methylheptoxy in the molecule have been proposed as a ferroelectric liquid crystal compound.

However, these ester compounds are available only within a restricted range of temperature.

SUMMARY OF THE INVENTION

It is the object of the present invention to provide an optically active compound useful as a ferroelectric liquid crystal compound.

The present invention provides a compound of the following general formula (I).

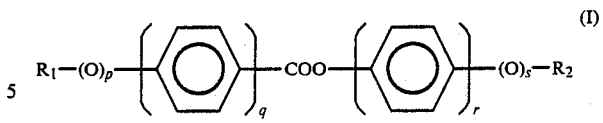

wherein p is zero or one; q and r are one or two and q+r is 3; s is zero or one; $R_1$ and $R_2$ are normal alkyl group having from one to 18 carbon atoms or optically active group of the formula

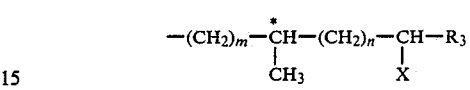

and at least one of $R_1$ and $R_2$ is optically active group; m is 2 to 5; n is one or two; X is hydrogen atom or chlorine atom; $R_3$ is hydrogen atom or normal alkyl group having from one to 11 carbon atoms and when n is one and X is hydrogen atom, $R_3$ is normal alkyl group having from one to 11 carbon atoms; and C* represents an asymmetric carbon atom.

DETAILED DESCRIPTION OF THE INVENTION

The compound of the present invention as represented by the above general formula (I) can be prepared by conventional method.

For example, it may be prepared by reacting 4-alkyl- or 4-alkoxy-benzoic acid with 4-alkyl- or 4-alkoxy-biphenol; or by reacting 4-alkyl- or 4-alkoxy-biphenylcarboxylic acid with 4-alkyl- or 4-alkoxy-phenol.

The obtained ester compound of the present invention as represented by the above general formula can be used alone as a liquid crystal material. Alternatively it can be mixed with other liquid crystal compound(s).

To further illustrate the present invention, the following Examples will be given.

EXAMPLE 1

Synthesis of (S)-4-n-octoxybiphenylcarboxylic acid 4-(4'-methylheptyloxy)phenyl ester

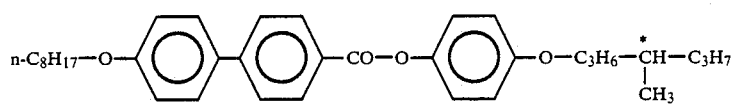

0.65 g of 4-n-octoxybiphenylcarboxylic acid, 0.44 g of (S)-4-(4'-methylheptyloxy)phenol, 0.41 g of N,N'-dicyclohexyl carbodiimide and 10 ml of dichloromethane were stirred for 3 hours at room temperature.

The precipitated N,N'-dicyclohexylurea were filtered and the filtrate was evaporated.

The product was purified on a silica gel column with the use of hexane/ether (9/1) as a developing solvent. Thus (S)-4-n-octoxybiphenylcarboxylic acid 4-(4'-methylheptyloxy)phenyl ester was obtained.

Infrared spectroscopy $(cm^{-1})$ 2900(s), 2850(s), 1720(s), 1600(s), 1500(s), 1460(m), 1270(s), 1240(s), 1190(vs), 1070(vs), 820(s) and 760(s)

Optical rotation $[\alpha]_D = +1.02°$ (C=1, $CHCl_3$ solution, 24° C.)

This compound was poured into a transparent glass cell and the following phase transition was observed under a polarization microscope.

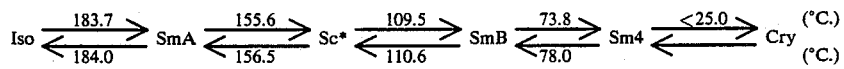

Iso: isotropic
Sc*: chiral smectic
SmA, SmB, Sm4: smectic
Cry: crystal

The phase transition of the compound where optically active group is 2-methylbutyl group and having the following formula is shown below:

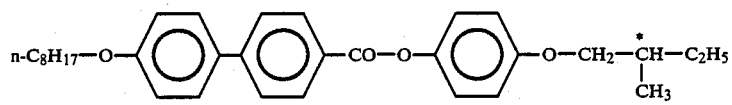

Phase transition:

It has been confirmed that the compound of present invention shows not only Sc* but other liquid crystal phase over a very wide temperature range, which obviously suggests that it is suitable for the preparation of a ferroelectric liquid crystal composition.

EXAMPLE 2

Synthesis of (S)-4-(4'-methyloctoxy)biphenylcarboxylic acid 4-n-hexyloxyphenyl ester

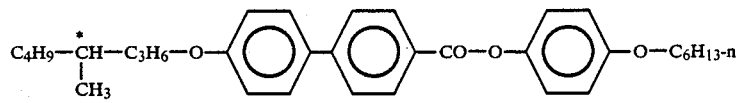

The procedure of Example 1 was followed except that the 4-n-octoxybiphenylcarboxylic acid and 4-(4'-methylheptyloxy)phenol were replaced by 4-(4'-methyloctoxy) biphenylcarboxylic acid and 4-n-hexyloxyphenol and the title compound was obtained.

Infrared spectroscopy (cm$^{-1}$) 2900(s), 2850(s), 1720(s), 1600(s), 1490(m), 1460(m), 1280(vs), 1240(s), 1190(vs), 1070(m), 830(m) and 760(m)

Optical rotation $[\alpha]_D = +5.40°$ (C=0.5, CHCl$_3$ solution, 24° C.)

Phase transition

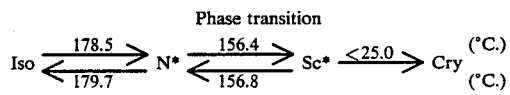

N*: chiral nematic

The phase transition of the compound where optically active group is 1-methylheptyl group and having the following formula is shown below:

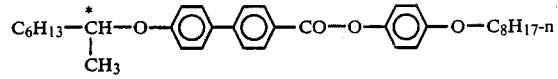

Phase transition:

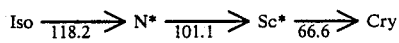

It has been confirmed that the compound of present invention shows not only Sc* but other liquid crystal phase over a very wide temperature range, which obviously suggests that it is suitable for the preparation of a ferroelectric liquid crystal composition.

EXAMPLE 3

Synthesis of (S)-4-(4'-methylheptyloxy) benzoic acid 4-n-octoxybiphenyl ester

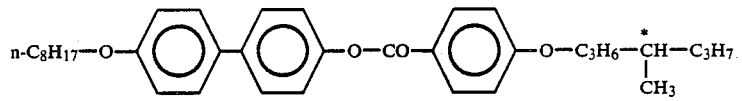

The procedure of Example 1 was followed using (S)-4(4'-methylheptyloxy)benzoic acid and 4-n-octoxybiphenyl and the title compound is obtained.

Infrared spectroscopy (cm$^{-1}$) 2900(s), 2850(s), 1720(s), 1600(s), 1490(s), 1460(m), 1250(vs), 1210(vs), 1160(vs), 1070(s), 840(m) and 760(m)

Optical rotation $[\alpha]_D = +1.34°$ (C=1, CHCl$_3$ solution, 24° C.)

Phase transition

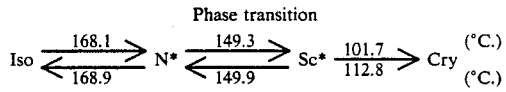

EXAMPLE 4

Synthesis of (S)-4-n-hexyloxybenzoic acid 4-(6'-methyldecyloxy)biphenyl ester

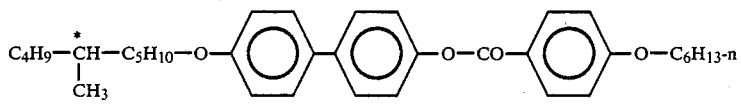

The procedure of Example 1 was followed using 4-n-hexyloxybenzoic acid and (S)-4-(6'-methyldecyloxy) biphenyl and the title compound is obtained.

Infrared spectroscopy (cm$^{-1}$) 2900(s), 2850(s), 1720(s), 1600(s), 1490(s), 1460(m), 1250(vs), 1200(vs), 1160(vs), 1070(s), 840(m) and 760(m)

Optical rotation $[\alpha]_D = +1.59°$ (C=1, CHCl$_3$ solution, 24° C.)

Phase transition

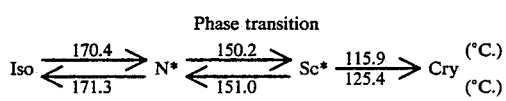

EXAMPLE 5

Synthesis of (S)-4-(5'-methyloctoxy)benzoic acid 4-n-octoxybiphenyl ester

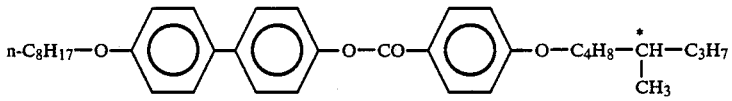

The procedure of Example 1 was followed using (S)-4-(5'-methyloctoxy)benzoic acid and 4-n-octoxybiphenyl and the title compound is obtained.

Infrared spectroscopy (cm$^{-1}$) 2900(s), 2850(s), 1720(s), 1600(s), 1490(s), 1460(m), 1250(vs), 1210(vs), 1160(vs), 1070(s), 840(m) and 760(m)

The precipitated N,N'-dicyclohexylurea were filtered and the filtrate was evaporated.

The product was purified by recrystallization from ethanol/acetone and the title compound was obtained.

Infrared spectroscopy (cm$^{-1}$) 3080(vw), 2950(s), 2880(m), 1735(s), 1610(s), 1585(vw), 1510(s), 1470(m), 1400(w), 1280(s), 1250(s), 1200(s), 1085(s), 1040(w), 1020(w), 875(w), 835(m), 770(m), 725(w), 700(w) and 530(w)

Phase transition

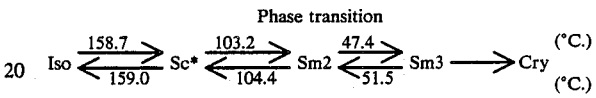

This compound was poured into a transparent glass electrode cell of 2 μm in thickness, which had been subjected to orientation by rubbing, and heated to 180° C. to thereby give an isotropic liquid. The liquid crystal cell thus obtained was cooled under a crossed Nicol prism while applying rectangular pulses (15 V. 1 Hz) thereto. As a result, definite switching behaviors were observed.

Spontaneous polarization: 1.7 nc/cm$^2$

The time between 90% and 0% transmission: 200 μsec.

EXAMPLE 7

Synthesis of (R)-4-(6'-chloro-3'-methylhexyloxy) biphenylcarboxylic acid 4-n-decyloxyphenyl ester

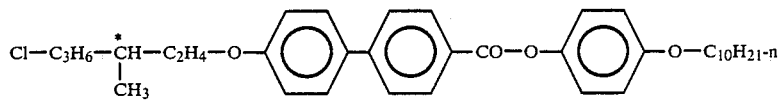

0.35 g of (R)-4-(6'-chloro-3'-methylhexyloxy)biphenyl carboxylic acid, 0.25 g of 4-n-decyloxyphenol, 0.21 g of N,N'-dicyclohexyl carbodiimide, 0.02 g of 4-pyrolidinopyridine and 10 ml of dichloromethane were stirred for 3 hours at room temperature.

The precipitated N,N'-dicyclohexyl urea were filtered and the filtrate was evaporated.

The product was purified on a silica gel column with the use of hexane/dichloromethane (1/1) as a developing solvent. Thus (R)-4-(6'-chloro-3'-methylhexyloxy)-biphenyl carboxylic acid 4-n-decyloxyphenyl ester was obtained.

Phase transition

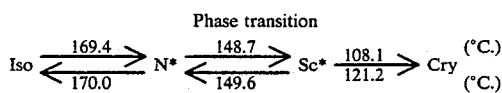

EXAMPLE 6

Synthesis of (R)-4-n-octoxybiphenylcarboxylic acid 4-(6'-chloro-4'-methyldecyloxy)phenyl ester

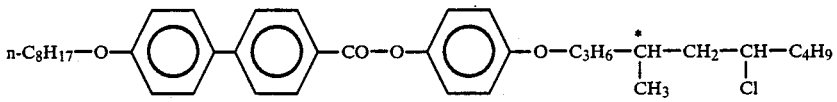

0.65 g of 4-n-octoxybiphenylcarboxylic acid, 0.60 g of (R)-4-(6'-chloro-4'-methyldecyloxy)phenol, 0.04 g of N,N'-dicyclohexyl carbodiimide and 20 ml of dichloromethane were stirred for 3 hours at room temperature.

Infrared spectroscopy (cm$^{-1}$) 3080(vw), 2950(s), 2880(m), 1740(s), 1610(s), 1585(vw), 1515(s), 1480(m), 1400(w), 1300(s), 1260(s), 1215(s), 1090(m), 1035(w), 880(w), 835(m), 775(m), 725(w), 700(w) and 530(w)

Phase transition

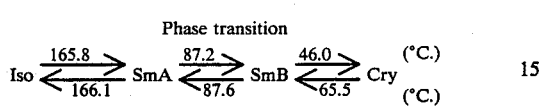

EXAMPLE 8

Synthesis of (R)-4-(6'-chloro-4'-methyloctoxy) benzoic acid 4-n-octoxybiphenyl ester

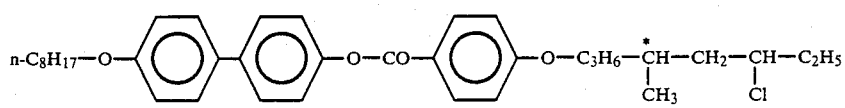

0.60 g of (R)-4-(6'-chloro-4'-methyloctoxy)benzoic acid, 0.60 g of 4-n-octoxybiphenol, 0.41 g of N,N'-dicyclohexyl carbodiimide, 0.04 g of 4-pyrolidinopyridine and 20 ml of dichloromethane were stirred for 3 hours at room temperature. The precipitated N,N'-dicyclohexyl urea were filtered and the filtrate was evaporated. Thus (R)-4-(6'-chloro-4'-methyloctoxy) benzoic acid 4-n-octoxybiphenyl ester was obtained.

Infrared spectroscopy (cm$^{-1}$) 3060(vw), 2950(s), 2875(m), 1730(s), 1610(s), 1580(w), 1510(m), 1500(m), 1470(m), 1425(w), 1385(w), 1260(s), 1215(s), 1175(s), 1080(m), 1005(w), 970(w), 890(w), 850(m), 810(m), 770(m), 700(w), 655(w) and 520(w)

Phase transition

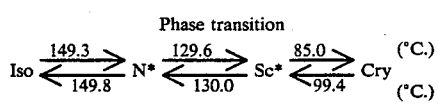

This compound was poured into a transparent glass electrode cell of 2 μm in thickness, which had been subjected to orientation by rubbing, and heated to 180° C. to thereby give an isotropic liquid.

The liquid crystal cell thus obtained was cooled under a crossed Nicol prism while applying rectangular pulses (15 V. 1 Hz) thereto. As a result, definite switching behaviors were observed.
Spontaneous polarization: 12.8 nc/cm$^2$
The time between 90% and 0% transmission: 350 μsec.

EXAMPLE 9

Synthesis of (R)-4-n-hexyloxybenzoic acid 4-(6'-chloro-4'-methylhexyloxy)biphenyl ester

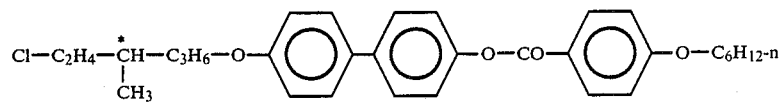

0.44 g of n-hexyloxybenzoic acid, 0.64 g of (R)-4-(6'-chloro-4'-methylhexyloxy)biphenol, 0.41 g of N,N'-dicyclohexylcarbodiimide, 0.04 g of 4-pyrolidinopyridine and 20 ml of dichloromethane were stirred for 3 hours at room temperature. The precipitated N,N'-dicyclohexyl urea were filtered and the filtrate was evaporated. Thus (R)-4-n-hexyloxy-benzoic acid 4-(6'-chloro-4'-methylhexyloxy)biphenyl ester was obtained.

Infrared spectroscopy (cm$^{-1}$) 3060(vw), 2950(m), 2890(w), 1730(s), 1610(s), 1580(w), 1500(s), 1470(m), 1425(w), 1390(w), 1260(s), 1215(s), 1175(s), 1080(m), 1005(m), 940(w), 885(w), 850(m), 815(m), 770(m), 700(w), 655(m) and 520(w)

Phase transition

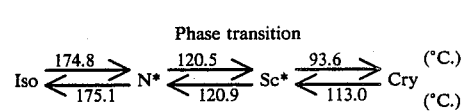

EXAMPLE 10

Synthesis of (S)-4-(4'-methyloctoxy)biphenyl carboxylic acid 4-n-octylphenyl ester

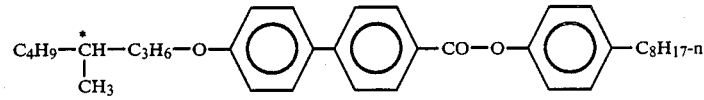

0.34 g of (S)-4-(4'-methyloctoxy)biphenyl carboxylic acid, 0.21 g of 4-n-octylphenol, 0.21 g of N,N'-dicyclohexyl carbodiimide, 0.02 g of 4-pyrolidinopyridine and 10 ml of dichloromethane were stirred for 3 hours at room temperature. The precipitated N,N'-dicyclohexyl urea were filtered and the filtrate was evaporated.

The product was purified on a silica gel column with the use of hexane/diethylether (95/5) as a developing solvent and (S)-4-(4'-methyloctoxy)biphenyl carboxylic acid 4-n-octyl-phenyl ester was obtained.

Infrared spectroscopy (cm$^{-1}$) 3050(vw), 2930(s), 2860(m), 1730(s), 1605(s), 1580(w), 1525(vw), 1510(m), 1470(m), 1425(vw), 1400(vw), 1380(vw), 1300(w), 1275(s), 1250(w), 1210(w), 1195(s), 1170(w), 1120(vw), 1075(s), 1020(w), 1000(vw), 925(vw), 885(w), 830(m), 770(m), 725(w), 700(w), 635(vw) and 500(vw)

Phase transition

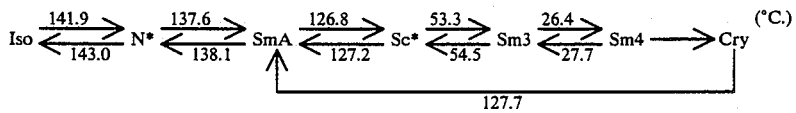

This compound was poured into a transparent glass electrode cell of 2 μm in thickness, which had been subjected to orientation by rubbing, and heated to 180° C. to thereby give an isotropic liquid. The liquid crystal cell thus obtained was cooled under a crossed Nicol prism while applying rectangular pulses (15 V. 1 Hz) thereto. As a result, definite switching behaviors were observed.

Spontaneous polarization: 3.0 nc/cm² (at 80° C.)
The time between 90% and 0% transmission: 1.3 msec. (at 80° C.)

EXAMPLE 11

Synthesis of (S)-4-(5'-methylnonyloxy) biphenyl carboxylic acid 4-n-octylphenyl ester

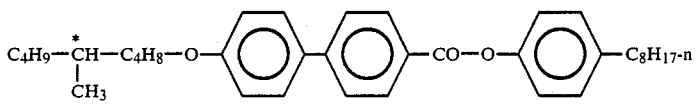

The procedure of Example 10 was followed except that the (S)-4-(4'-methyloctoxy)biphenylcarboxylic acid was replaced by (S)-4-(5'-methylnonyloxy)biphenylcarboxylic acid and the title compound was obtained after purified on a silica gel column with the use of hexane/dichloromethane (7/3) as a developing solvent.

Infrared spectroscopy (cm⁻¹) 3050(vw), 2930(s), 2860(m), 1730(s), 1605(s), 1580(vw), 1530(vw), 1510(m), 1465(m), 1430(vw), 1400(vw), 1380(vw), 1290(s), 1280(m), 1255(w), 1200(s), 1175(w), 1140(vw), 1080(s), 1035(vw), 1020(w), 1000(vw), 940(vw), 830(m), 770(m), 720(w), 695(vw), 630(vw) and 515(w)

Phase transition

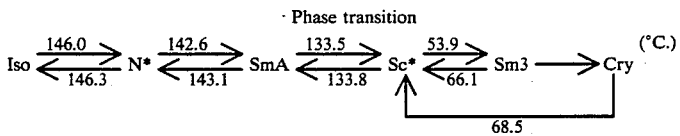

This compound was poured into a transparent glass electrode cell of 2 μm in thickness, which had been subjected to orientation by rubbing, and heated to 180° C. to thereby give an isotropic liquid. The liquid crystal cell thus obtained was cooled under a crossed Nicol prism while applying rectangular pulses (15 V. 1 Hz) thereto. As a result, definite switching behaviors were observed.

Spontaneous polarization: 1.4 nc/cm² (at 80° C.)
The time between 90% and 0% transmission: 270 μsec. (at 80° C.)

EXAMPLE 12

Synthesis of (S)-4-(5'-methylnonyl)benzoic acid 4-n-octoxybiphenyl ester

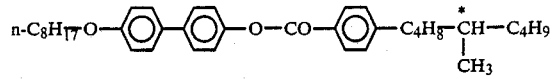

The procedure of Example 10 was followed except that the (S)-4-(4'-methyloctoxy)biphenyl carboxylic acid and 4-n-octylphenol were replaced by (S)-4-(5'-methylnonyl)benzoic acid and 4-n-octoxybiphenol to thereby give the title compound. The product was purified on a silica gel column with the use of hexane/dichloromethane (95/5) as a developing solvent.

Infrared spectroscopy (cm⁻¹) 3050(vw), 2930(s), 2860(m), 1735(s), 1605(s), 1570(vw), 1495(s), 1465(m), 1415(vw), 1380(w), 1270(s), 1215(s), 1180(m), 1170(m), 1120(vw), 1080(s), 1020(w), 1000(vw), 970(w), 885(w), 840(m), 805(m), 760(w), 745(w), 725(vw), 645(vw) and 515(w)

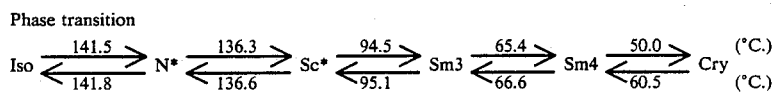

This compound was poured into a transparent glass electrode cell of 2 μm in thickness, which had been subjected to orientation by rubbing, and heated to 180° C. to thereby give an isotropic liquid. The liquid crystal cell thus obtained was cooled under a crossed Nicol prism while applying rectangular pulses (15 V. 1 Hz) thereto. As a result, definite switching behaviors were observed.

The time between 90% and 0% transmission: 300 μsec.

EXAMPLE 13

Synthesis of (S)-4-n-octylbenzoic acid 4-(4'-methyloctoxy)biphenyl ester

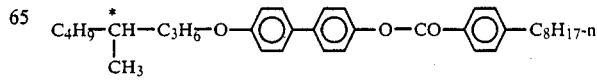

0.23 g of 4-n-octylbenzoic acid, 0.31 g of (S)-4-(4'-methyloctoxy)biphenol, 0.21 g of N,N'-dicyclohexyl carbodiimide, 0.02 g of 4-pyrolidinopyridine and 10 ml of dichloromethane were stirred for 3 hours at room temperature.

The precipitated N,N'-dicyclohexyl urea were filtered and the filtrate was evaporated.

The product was purified on a silica gel column with the use of hexane/diethylether (95/5) as a developing solvent and (S)-4-n-octylbenzoic acid 4-(4'-methyloctoxy) biphenyl ester was obtained.

Infrared spectroscopy (cm$^{-1}$) 3050(vw), 2930(s), 2860(m), 1735(s), 1610(s), 1575(vw), 1495(s), 1470(m), 1415(vw), 1380(w), 1270(s), 1215(s), 1180(m), 1170(m), 1120(vw), 1080(s), 1020(w), 1000(w), 930(vw), 885(w), 840(m), 810(m), 760(w), 730(vw), 640(vw) and 520(w)

Phase transition $$Iso \underset{140.0}{\overset{140.7}{\rightleftarrows}} N^* \underset{126.5}{\overset{126.3}{\rightleftarrows}} Sc^* \underset{78.0}{\overset{76.5}{\rightleftarrows}} Sm3 \underset{59.0}{\overset{57.4}{\rightleftarrows}} Sm4 \longrightarrow Cry \quad (°C.)$$

This compound was poured into a transparent glass electrode cell of 2 μm in thickness, which had been subjected to orientation by rubbing, and heated to 180° C. to thereby give an isotropic liquid. The liquid crystal cell thus obtained was cooled under a crossed Nicol prism while applying rectangular pulses (15 V. 1 Hz) thereto. As a result, definite switching behaviors were observed.

The time between 90% and 0% transmission: 500 μsec.

EXAMPLE 14

Synthesis of (R)-4-n-octylbenzoic acid 4-(6'-chloro-4'-methylhexyloxy)biphenyl ester

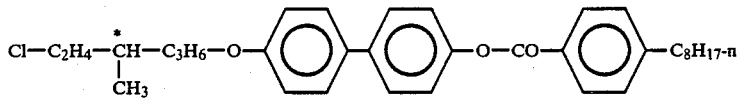

The procedure of Example 13 was followed except that the (S)-4-(4'-methyloctoxy)biphenol was replaced by (R)-4-(6'-chloro-4'-methylhexyloxy)biphenol to thereby give the title compound.

The product was purified on a silica gel column with the use of hexane/diethylether (9/1) as a developing solvent.

Infrared spectroscopy (cm$^{-1}$) 3050(vw), 2940(s), 2860(m), 1735(s), 1605(s), 1570(vw), 1495(s), 1470(m), 1415(vw), 1380(w), 1270(s), 1215(s), 1180(m), 1170(m), 1120(vw), 1075(s), 1020(w), 1000(w), 920(vw), 885(w), 840(m), 805(m), 760(w), 730(w), 640(vw), and 515(w).

Phase transition

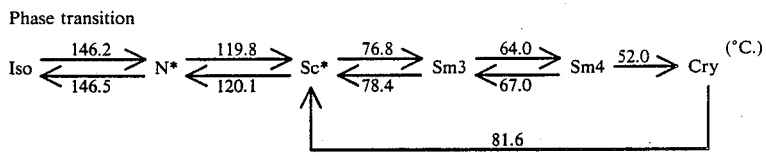

This compound was poured into a transparent glass electrode cell of 2 μm in thickness, which had been subjected to orientation by rubbing, and heated to 180° C. to thereby give an isotropic liquid. The liquid crystal cell thus obtained was cooled under a crossed Nicol prism while applying rectangular pulses (15 V. 1 Hz) thereto. As a result, definite switching behaviors were observed.

Spontaneous polarization: 1.4 nc/cm$^2$ (at 80° C.)
The time between 90% and 0% transmission: 240 μsec. (at 100° C.)

EXAMPLE 15

Synthesis of (R)-4-n-octylbenzoic acid 4-(6'-chloro-4'-methyloctoxy)biphenyl ester

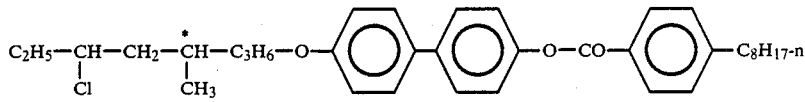

The procedure of Example 13 was followed except that the (S)-4-(4'-methyloctoxy)biphenol was replaced by (R)-4-(6'-chloro-4'-methyloctoxy)biphenol to thereby give the title compound.

The product was purified on a silica gel column with the use of hexane/diethylether (9/1) as a developing solvent.

Infrared spectroscopy (cm$^{-1}$) 3050(vw), 2930(s), 2860(m), 1735(s), 1605(s), 1570(vw), 1495(s), 1465(m), 1415(vw), 1380(w), 1270(s), 1215(s), 1180(m), 1170(m), 1120(vw), 1075(m), 1020(w), 1000(w), 930(vw), 885(w), 830(m), 805(m), 740(w), 700(vw), 640(vw) and 520(vw)

Phase transition

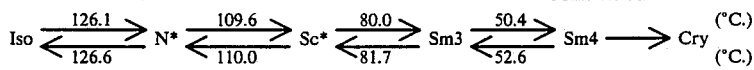

This compound was poured into a transparent glass eletrode cell of 2 μm in thickness, which had been subjected to orientation by rubbing, and heated to 160° C. to thereby give an isotropic liquid. The liquid crystal cell thus obtained was cooled under a crossed Nicol prism while applying rectangular pulses (15 V. 1 Hz) thereto. As a result, definite switching behaviors were observed.

Spontaneous polarization: 18.2 nc/cm²

The time between 90% and 0% transmission: 230 μsec. (at 100° C.)

What is claimed is:

1. An optically active ester of the formula

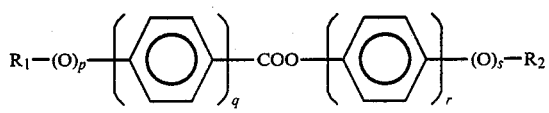

wherein p is 0 or 1, q is 1 or 2, r is 1 or 2, q+r is 3, s is 0 or 1, and $R_1$ and $R_2$ are each independently selected from the group consisting of $C_{6-18}$ straight chain alkyl and an optically active group of the formula

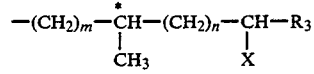

and in which m is 2 to 5, n is 1 or 2, X is hydrogen or chlorine, $R_3$ is hydrogen or $C_{1-11}$ straight chain alkyl, and C* represents a chiral carbon atom, and when n is 1 and X is hydrogen, $R_3$ is $C_{1-11}$ straight chain alkyl; one of $R_1$ and $R_2$ being a said optically active group and the other of $R_1$ and $R_2$ being a said $C_{6-18}$ straight chain alkyl group; and when q is 2 and r is 1 and $R_1$ is $C_{6-18}$ straight chain alkyl, p is 1; and when q is 1 and r is 2 and $R_2$ is a said optically active group, s is 1.

2. An ester according to claim 1, wherein q is 1 and r is 2.

3. An ester according to claim 1, wherein q is 2 and r is 1.

4. An ester according to claim 1, wherein $R_1$ is a said optically active group and $R_2$ is a said $C_{6-18}$ straight chain alkyl group.

5. An ester according to claim 1, wherein $R_1$ is a said $C_{6-18}$ straight chain alkyl group and $R_2$ is a said optically active group.

6. An ester according to claim 1, wherein p is 1 and s is 1.

7. An ester according to claim 1, wherein p is 1 and s is 0.

8. An ester according to claim 1, wherein p is 0 and s is 1.

9. An ester according to claim 1, wherein X is hydrogen.

10. An ester according to claim 1, wherein X is chlorine.

* * * * *